United States Patent
Gotman et al.

(10) Patent No.: US 10,820,865 B2
(45) Date of Patent: Nov. 3, 2020

(54) SPECTRAL COMPUTED TOMOGRAPHY FINGERPRINTING

(71) Applicants: KONINKLIJKE PHILIPS N.V., Eindhoven (NL); BOARD OF REGENTS, THE UNIVERSITY OF TEXAS SYSTEM, Dallas, TX (US)

(72) Inventors: Shlomo Gotman, Haifa (IL); Liran Goshen, Pardes-Hanna (IL); Robert E. Lenkinski, Dallas, TX (US); Matthew A. Lewis, Dallas, TX (US); Todd C. Soesbe, Dallas, TX (US); Duan Xinhui, Dallas, TX (US)

(73) Assignee: KONINKLIJKE PHILIOPS N.V., Eindhoven (NL)

( * ) Notice: Subject to any disclaimer, the term of this patent is extended or adjusted under 35 U.S.C. 154(b) by 4 days.

(21) Appl. No.: 16/316,735

(22) PCT Filed: Jul. 12, 2017

(86) PCT No.: PCT/EP2017/067644
§ 371 (c)(1),
(2) Date: Jan. 10, 2019

(87) PCT Pub. No.: WO2018/011321
PCT Pub. Date: Jan. 18, 2018

(65) Prior Publication Data
US 2019/0290226 A1    Sep. 26, 2019

Related U.S. Application Data

(60) Provisional application No. 62/361,702, filed on Jul. 13, 2016.

(51) Int. Cl.
*A61B 6/03* (2006.01)
*A61B 6/00* (2006.01)
*G06T 7/00* (2017.01)

(52) U.S. Cl.
CPC ............ *A61B 6/032* (2013.01); *A61B 6/4241* (2013.01); *A61B 6/469* (2013.01); *A61B 6/482* (2013.01);
(Continued)

(58) Field of Classification Search
CPC ....... A61B 6/032; A61B 6/4241; A61B 6/482; A61B 6/463; A61B 6/5211; G06T 7/0012; G06T 2207/10081
See application file for complete search history.

(56) References Cited

U.S. PATENT DOCUMENTS

2007/0189443 A1    8/2007   Walter
2008/0253504 A1   10/2008   Proksa
(Continued)

FOREIGN PATENT DOCUMENTS

JP    2011110245    6/2011
WO    2016059527   4/2016

OTHER PUBLICATIONS

Badve, et al., "Magnetic Resonance Fingerprinting of Brain Tumors: Initial Clinical Results", Neuro-Oncology 16:v138-v158, 2014, Abstract.
(Continued)

*Primary Examiner* — Courtney D Thomas
(74) *Attorney, Agent, or Firm* — Larry Liberchuk

(57) ABSTRACT

A method includes generating spectral projection data of a subject, including at least first spectral projection data corresponding to a first energy range and second spectral projection data corresponding to a second energy range, wherein the first and the second energy range are different. The method further includes constructing an image from a combination of the spectral projection data, and constructing a set of basis images for the 5 energy ranges and from the spectral projection data. The method further includes constructing a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material 10 represented in the spectral projection data. The method further includes visually presenting, concurrently, the image and the multi-dimensional histogram.

23 Claims, 14 Drawing Sheets

(52) U.S. Cl.
CPC ............ *G06T 7/0012* (2013.01); *A61B 6/463* (2013.01); *A61B 6/5211* (2013.01); *G06T 2207/10081* (2013.01)

(56) References Cited

U.S. PATENT DOCUMENTS

| | | | |
|---|---|---|---|
| 2010/0128844 A1* | 5/2010 | Thomsen | A61B 6/032 378/53 |
| 2010/0328313 A1 | 12/2010 | Zamyatin | |
| 2012/0106816 A1 | 5/2012 | Bernard | |
| 2015/0161787 A1 | 6/2015 | Li | |
| 2015/0161792 A1 | 6/2015 | Li | |

OTHER PUBLICATIONS

Boone, et al., "Comparison of x-ray cross sections for diagnostic and therapeutic medical physics." Medical Physics Dec. 23, 1996.
Brody, et al., "Dual-KVp Radiography: Initial Clinical Experience" American Journal of Roentgenology 136(6): 1277-1277., 1981.
Jiang, et al., "MR Fingerprinting Using Fast Imaging with Steady State Precession (FISP) with Spiral Readout" Magnetic Resonance in Medicine 74:1621-1631 (2015).
Chen, et al., "MR Fingerprinting for Rapid Quantitative Abdominal Imaging1", Radiology: vol. 279: No. 1—Apr. 2016.
Lehmann, et al., "Generalized Image Combinations in Dual KVp Digital Radiography." Medical Physics 8(5): 659-667, Oct. 1981.
Ma, et al., "Magnetic resonance fingerprinting", Nature 495(7440): 187-192, Mar. 14, 2013.
Riederer, et al., "Beam Hardening, Noise, and Contrast Considerations in Selective Iodine Digital Radiography", IEEE Transactions on Nuclear Science, vol. NS-28, No. 1, Feb. 1981.
Pelc, N. J., et al. (1981). "Dual Energy Digital Radiography." Journal of Computer Assisted Tomography 5(6): 944-945.
Houndfield, G. N. (1973). "Computerized Transverse Axial Scanning (Tomography) .1. Description of System." British Journal of Radiology 46(552): 1016-1022.
Brody, W. R., et al. (1981). "Dual-KVp Radiography." Proceedings of the Society of Photo-Optical Instrumentation Engineers 273: 239-243.

* cited by examiner

SPECTRAL COMPUTED TOMOGRAPHY FINGERPRINTING

CROSS REFERENCE TO RELATED APPLICATIONS

This application is the U.S. National Phase application under 35 U.S.C. § 371 of International Application No. PCT/EP2017/067644 filed Jul. 12, 2017, published as WO 2018/011321 on Jan. 18, 2018, which claims the benefit of U.S. Provisional Patent Application No. 62/361,702 filed Jul. 13, 2016. These applications are hereby incorporated by reference herein.

FIELD OF THE INVENTION

The following generally relates to spectral imaging and more particularly to spectral computed tomography (CT) fingerprinting.

BACKGROUND OF THE INVENTION

A CT scanner generally includes an x-ray tube mounted on a rotatable gantry opposite one or more integrating detectors. The x-ray tube rotates around an examination region located between the x-ray tube and the one or more detectors and emits radiation that traverses the examination region and a subject and/or object disposed in the examination region. The one or more detectors detect radiation that traverses the examination region and generate a signal or projection data indicative of the examination region and the subject and/or object disposed therein.

The projection data is reconstructed to generate volumetric image data, which can be used to generate one or more images. The resulting image(s) includes pixels that are represented in terms of gray scale values corresponding to relative radiodensity. Such information reflects the attenuation characteristics of the scanned subject and/or object, and generally shows structure such as anatomical structures within a patient, physical structures within an inanimate object, and the like. These images are highly dependent on the X-ray source and properties of the photon detectors.

The detected radiation also includes spectral information since the absorption of the radiation by the subject and/or object is dependent on the energy of the photons traversing there through. Such spectral information provides additional information such as information indicative of elemental or material composition (e.g., atomic number) of tissue and/or a material of the subject and/or object. However, with conventional CT, the projection data does not reflect the spectral characteristics as the data it represents is proportional to the energy fluence integrated over the energy spectrum.

A CT scanner configured for spectral (multi-energy) imaging leverages the spectral characteristics. For example, with a dual energy system, basis images reflecting intrinsic properties of a material being imaged (e.g., the photoelectric effect (PE) and Compton scattering (CS) behavior of each component of the tissue) can be generated. Although such images allow discrimination of materials based on energy attenuation characteristics, they are not well-suited to identify a presence or absence of a particular type of material such as identifying normal and/or diseased tissue of a particular type of tissue.

SUMMARY OF THE INVENTION

Aspects described herein address the above-referenced problems and others.

In one aspect, a method includes generating spectral projection data of a subject, including at least first spectral projection data corresponding to a first energy range and second spectral projection data corresponding to a second energy range, wherein the first and the second energy range are different. The method further includes constructing an image from a combination of the spectral projection data, and constructing a set of basis images for the energy ranges and from the spectral projection data. The method further includes constructing a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data. The method further includes visually presenting, concurrently, the image and the multi-dimensional histogram In another aspect, a system includes a memory storing instructions, including a spectral CT fingerprint module and a processor configured to execute at least instructions corresponding to the spectral CT fingerprint module. The instructions cause the processor to: generate spectral projection data of a subject, including at least first spectral projection data corresponding to a first energy range and second spectral projection data corresponding to a second energy range, wherein the first and the second energy range are different, construct an image from a combination of the spectral projection data, construct a set of basis images for the energy ranges and from the spectral projection data, construct a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data, and visually present, concurrently, the image and the multi-dimensional histogram.

In another aspect, a computer readable medium is encoded with computer executable instructions, which, when executed by a processor of a computer, cause the processor to: generate spectral projection data of a subject, including at least first spectral projection data corresponding to a first energy range and second spectral projection data corresponding to a second energy range, wherein the first and the second energy range are different, construct an image from a combination of the spectral projection data, construct a set of basis images for the energy ranges and from the spectral projection data, construct a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data, and visually present, concurrently, the image and the multi-dimensional histogram.

In another aspect, a method includes generating, with an imaging system, first spectral projection data representing known normal tissue for a predetermined type of tissue, including at least first spectral projection data corresponding to a first energy range and second spectral projection data corresponding to a second energy range, wherein the first and the second energy range are different. The method further includes generating, with the imaging system, second spectral projection data representing abnormal tissue for the predetermined type of tissue, including at least first spectral projection data corresponding to the first energy range and second spectral projection data corresponding to the second energy range. The method further includes constructing a first set of basis images for the energy ranges and from the first spectral projection data, and constructing a second set of basis images for the energy ranges and from the second spectral projection data. The method further includes constructing a first multi-dimensional histogram from the first set of basis images, wherein the first multi-dimensional histogram includes at least two axes, a first corresponding to a first basis component and a second corresponding to a second basis component, and constructing a second multi-dimensional histogram from the second set of basis images, wherein the second multi-dimensional histogram includes at least two axes, a first corresponding to the first basis component and a second corresponding to the second basis component. The method further includes identifying a cluster in the second multi-dimensional histogram that is absent from the first multi-dimensional histogram, labelling the identified cluster as representing the known abnormal tissue, and saving the first multi-dimensional histogram a spectral imaging fingerprint for the normal tissue and the second multi-dimensional histogram with the label as a spectral imaging fingerprint for the abnormal tissue.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
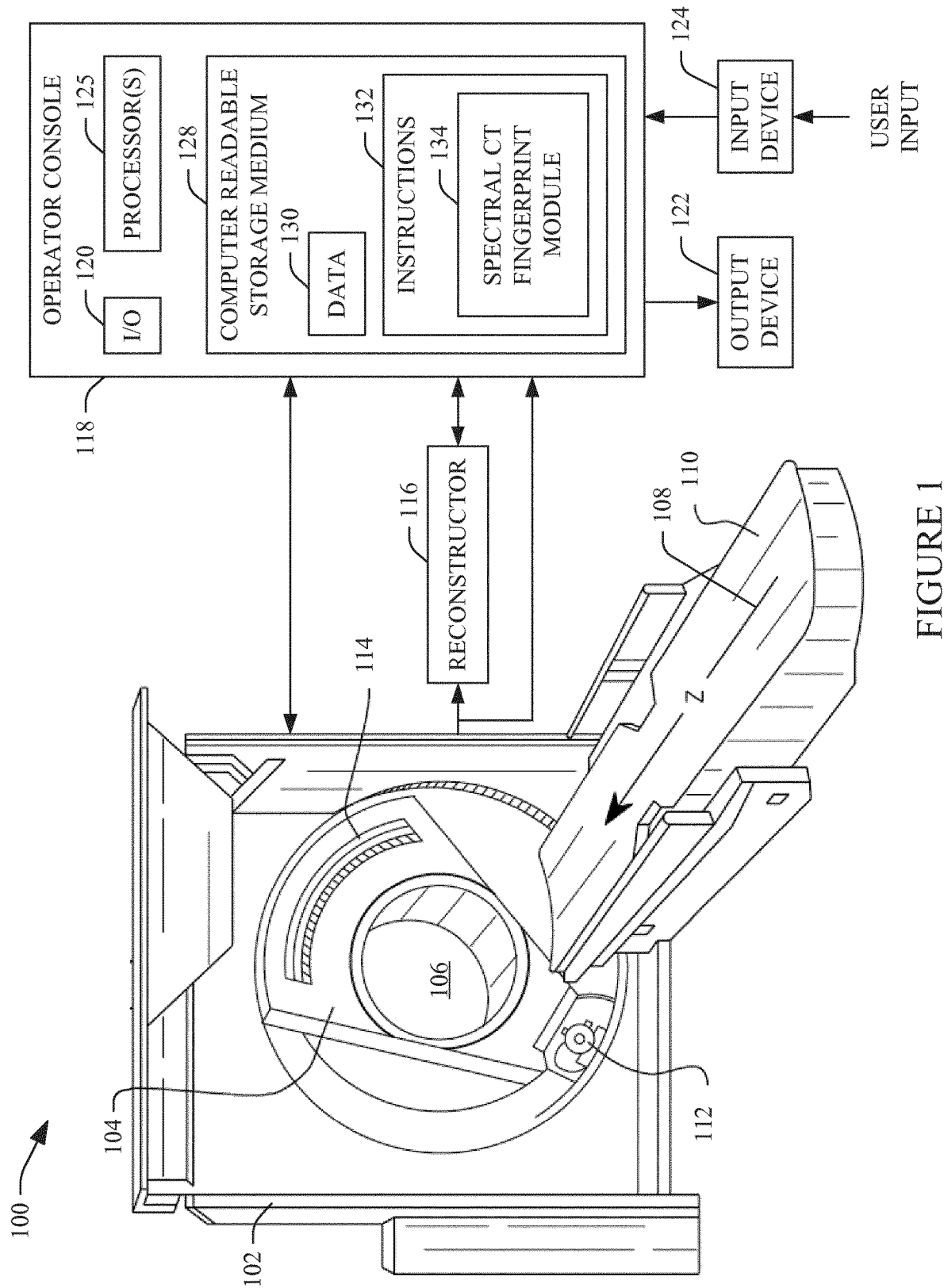
FIG. 1 schematically illustrates an imaging system including a console with a spectral CT fingerprint module.

FIG. 1 schematically illustrates an imaging system 100 such as a computed tomography (CT) scanner configured for spectral (multi-energy) imaging. The imaging system 100 includes a generally stationary gantry 102 and a rotating gantry 104. The rotating gantry 104 is rotatably supported by the stationary gantry 102 and rotates around an examination region 106 about a longitudinal or z-axis 108. A subject support 110, such as a couch, supports an object or subject in the examination region. The subject support 110 is movable in coordination with performing an imaging procedure so as to guide the subject or object with respect to the examination region 106 for loading, scanning, and/or unloading the subject or object.

A radiation source 112, such as an x-ray tube, is rotatably supported by the rotating gantry 104. The radiation source 112 rotates with the rotating gantry 104 and emits polychromatic radiation that traverses the examination region 106. In the illustrated embodiment, the radiation source 112 is a (standard) single x-ray tube configured to emit radiation for a single selected peak emission voltage (kVp) of interest (i.e. the energy spectrum at that kVp). In another instance, the radiation source 112 is configured to switch between at least two different emission voltages (e.g., 80 kVp, 140 kVp, etc.) during scanning In yet another instance, the radiation source 112 includes two or more x-ray tubes angular offset on the rotating gantry 104 with each configured to emit radiation with a different mean energy spectrum. U.S. Pat. No. 8,442,184 B2 to Koninklijke Philips Electronics N.V describes systems with kVp switching and multiple x-ray tubes.

A radiation sensitive detector array 114 subtends an angular arc opposite the radiation source 112 across the examination region 106. The detector array 114 includes one or more rows of detectors that arranged with respect to each other along the z-axis 108 direction and detects radiation traversing the examination region 106. In the illustrated embodiment, the detector array 114 includes an energy-resolving detectors such as a multi-layer scintillator/photosensor detector. U.S. Pat. No. 8,442,184 B2 and U.S. Pat. No. 7,968,853 B2, both to Koninklijke Philips Electronics N.V, describe a multi-layer detector. With an energy-resolving detector, the radiation source 112 includes the standard, the kVp switching and/or the multiple X-ray tube radiation source 112. In another instance, the detector array 114 includes a non-energy-resolving detector, and the radiation source 112 includes the kVp switching and/or the multiple X-ray tube radiation source 112. The detector array 114 generates and outputs a signal (projection data) indicative of each of N different energies, where N is an integer equal or greater than two.

Figure 2:
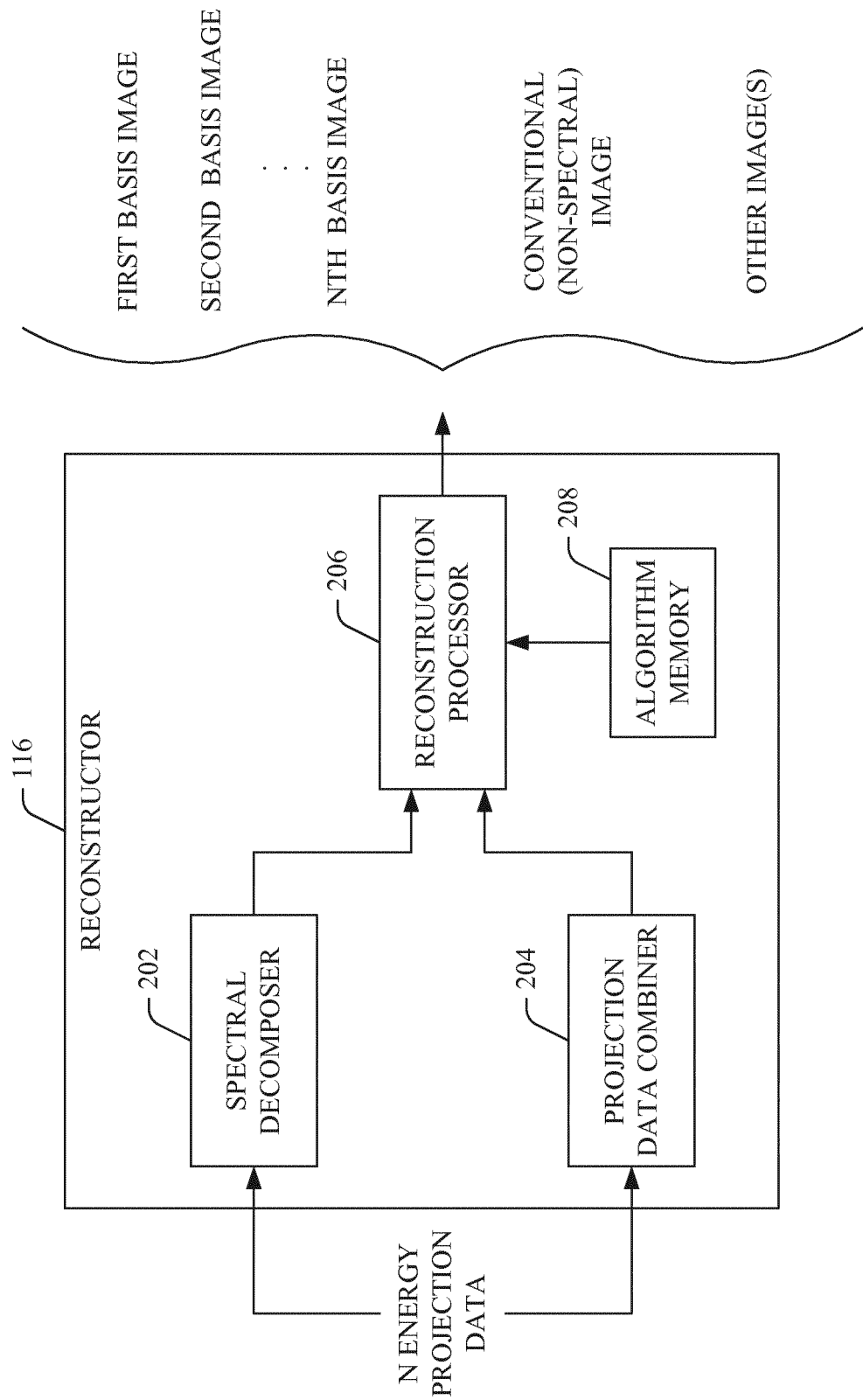
FIG. 2 schematically illustrates an example of a reconstructor of the imaging system.

A reconstructor 116 reconstructs the signals (projection data) output by the detector array 114. FIG. 2 schematically illustrates an example of the reconstructor 116. In this example, the reconstructor 116 receives projection data for each of the N different energies (N energy projection data). A spectral decomposer 202 decomposes the N different energies into different basis projection data, and a projection data combiner 204 combines the N different energies into different basis projection data. For example, for a dual energy (N=2), such as first (higher) and second (lower) energy, configuration, the spectral decomposer 202 decomposes the first and second energy projection data into photo-electric effect basis projection data and Compton scatter basis projection data. For this same case, the projection data combiner 204 combines the first and second energy projection data to produce combined data equivalent to non-spectral image data.

A reconstruction processor 206 reconstructs the basis projection data and/or the combined projection data based on reconstruction algorithms from algorithm memory 208. This may include reconstructing one or more basis images (e.g., a first basis image, a second basis image, . . . , and an Nth basis image). For example, for the dual energy example, the reconstruction processor 206 can generate a photo-electric effect image, a Compton scatter image, and/or a combination photo-electric effect/Compton scatter image. This may additionally include reconstructing a conventional (non-spectral) image from the combined projection image. Other image(s) which can be generated from this data include, but are not limited to, low and high energy images, a mono-energetic or monochrome image (e.g., 140 kVp), a virtual non-contrast (or unenhanced) image, an effective Z (atomic number) image, an iodine map, etc. The reconstructor 116 outputs the reconstructed images.

Returning to FIG. 1, an operator console 118 (computing system) allows an operator to control an operation of the system 100. This includes selecting an imaging acquisition protocol (e.g., multi-energy), selecting a reconstruction algorithm (e.g., multi-energy), invoking scanning, invoking a visualization software application, interacting with an executing visualization software application, etc. The operator console 118 includes input/output (I/O) 120 that facilitates communication with at least an output device(s) 122 such as a display monitor, a filmer, etc., an input device(s) 124 such as a mouse, keyboard, etc. The operator console 118 further includes at least one processor 125 (e.g., a central processing unit or CPU, a microprocessor, a controller, or the like) and a computer readable storage medium 126 (which excludes transitory medium), such as physical memory and/or other non-transitory memory. The computer readable storage medium 128 stores computer readable instructions 132 and data 130. The processor 125 executes the instructions 132.

The illustrated computer readable instructions 130 include at least a spectral CT fingerprint module 134. In one instance, the spectral CT fingerprint module 134 includes instructions for creating a material attenuation decomposition (MAD) plot (or histogram), which serves as a spectral CT fingerprint. Additionally, or alternatively, the spectral CT fingerprint module 128 includes instructions for employing such a MAD plot. A spectral CT fingerprint, as utilized herein, maps spectral CT data indicative of a particular type of tissue/material to that type of tissue/material. As such, the spectral CT fingerprint can be used to construct an image that visually emphasizes a particular type of tissue/material of interest. The spectral CT fingerprint can also be used to determine a presence or an absence of a particular type of tissue/material in an image. The spectral CT fingerprint can also be used to identify an unknown tissue/material in an image. The spectral CT fingerprint is system and energy invariant, and can be used with any CT imaging system. As such, it can also be used to confirm a CT imaging system is properly calibrated.

Figure 3:
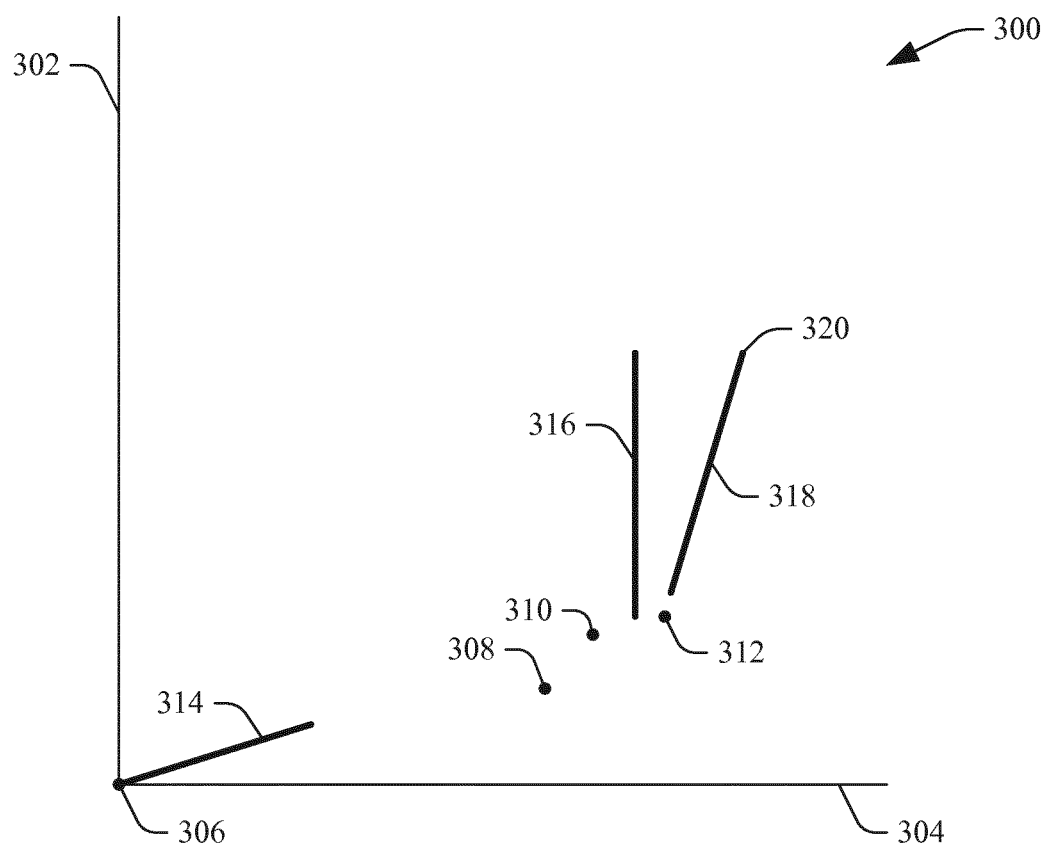
FIG. 3 graphically illustrates a theoretical material attenuation decomposition (MAD) plot for dual energy projection data.

FIG. 3 illustrates a theoretical MAD plot 300 for dual energy. A first (or y-) axis 302 represents a first basis and a second (or x-) axis represents a second basis. In the illustrated embodiment, the first axis 302 represents photo-electric effect attenuation coefficients and the second axis represents Compton scatter attenuation coefficients. In a variation, the coefficient values are dimensionless or have other units such as Hounsfield (HU). The photo-electric effect and Compton scatter attenuation coefficients can be obtained from basis images generated by the reconstructor 116. The materials represented in the MAD plot 300 are for explanatory purposes and are not limiting. Other materials, including fewer or more, similar or different, etc. may be represented in other MAD plots. Examples include two mono-energetic images, a low and high energy image pair, etc. Each basis in the MAD plot represents another dimension.

In the MAD plot 300, an origin 306 represents air. A first cluster 308 provides a spectral CT fingerprint for adipose tissue (fat). A second cluster 310 provides a spectral CT fingerprint for water. A third cluster 312 provides a spectral CT fingerprint for soft tissue. A fourth cluster 314 provides a spectral CT fingerprint for lung tissue. The fourth cluster 314 is spread over a range, e.g., due at least to partial volume effects with air and lung tissue. The fifth cluster 316 provides a spectral CT fingerprint for lung iodine. The fifth cluster 316 is spread over a range, e.g., as a function of a level of iodine concentration, with higher levels represented by high attenuation coefficient values on the first axis 302. The sixth cluster 318 provides a spectral CT fingerprint for calcium. The sixth cluster 318 is spread over a range, e.g., due at least to partial volume effects with bone and soft tissue. Pure calcium is represented in this range at 320.

Returning to FIG. 1, MAD plots can be generated for any number of tissues/materials. This includes generating a MAD plot for known normal tissue of a particular type and known abnormal tissue of a particular type. For example, a MAD plot can be generated from image data for a population of patients known to have a healthy liver (or other tissue), and another MAD plot can be generated from image data for a population of patients known to have a particular liver (or other tissue) tumor or lesion. The MAD plot can be for the entire body, a particular body part, and/or a particular organ. In another example, a MAD plot can be generated from image data from scanning a "phantom" constructed with a particular material (e.g., bone) and/or a known distribution of a particular material (e.g., a contrast agent). MAD plots can be stored locally (e.g., in the memory 128) and/or remotely (e.g., within a healthcare entity, on a server, in the "cloud," etc.).

MAD plots can be visually displayed, via a display monitor of the output device 124, concurrently with an image, individually, and/or alternately with an image. FIGS. 4-7 illustrate example visualization and use of MAD plots described herein. All of FIGS. 4-7 concurrently show an image and a MAD plot in a graphical user interface (GUI) of a display monitor of the output device 124.

Figure 4:
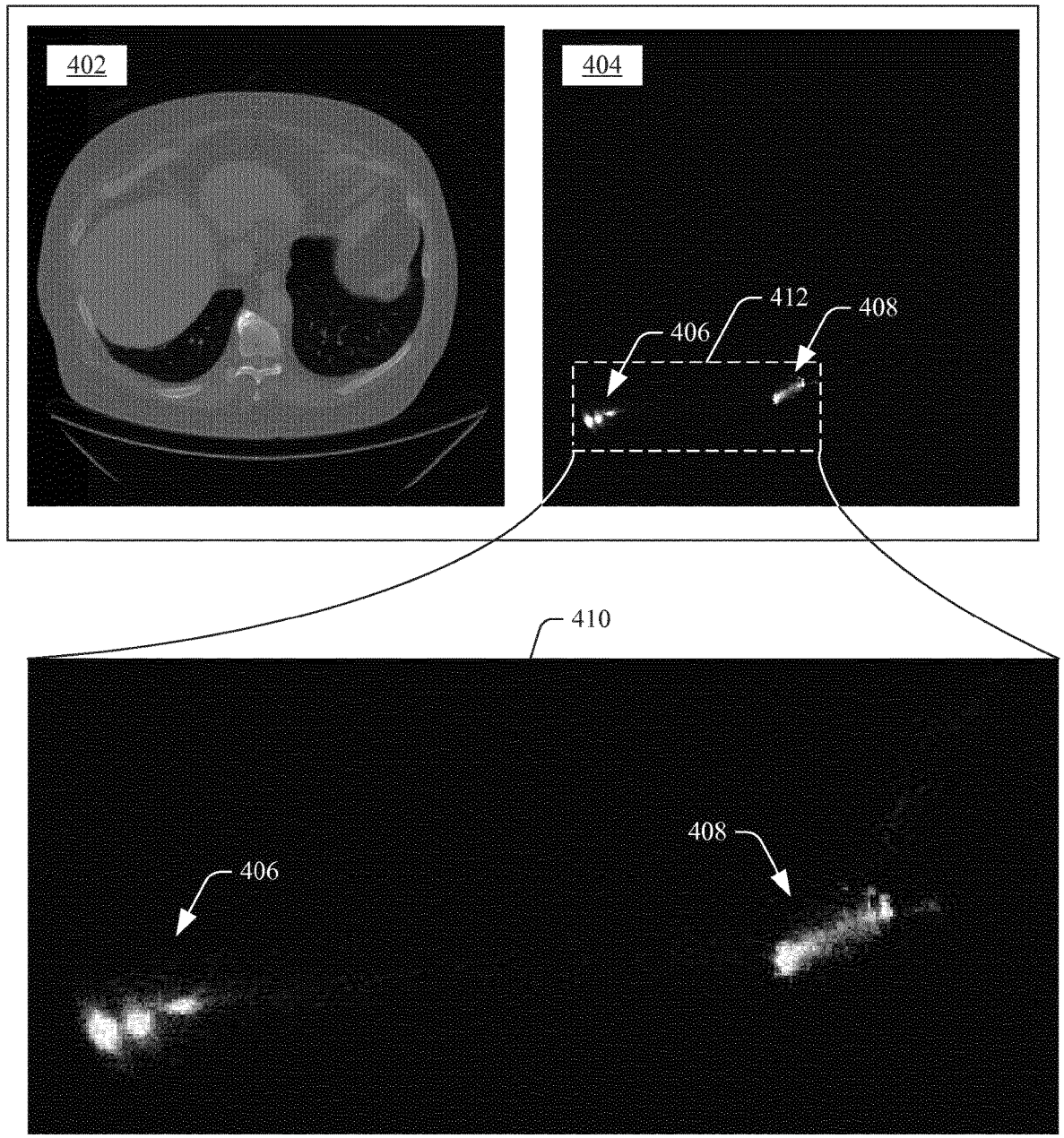
FIG. 4 depicts visual display of a 2-D image and a corresponding MAD plot.

FIG. 4 shows a 2-D image 402 and a corresponding MAD plot 404. The MAD plot 404 is created based on an entirety of the pixels or voxels of the 2-D image 402. Similar to the MAD plot 300 in FIG. 3, the MAD plot 404 is a photoelectric effect vs Compton scatter attenuation coefficient 2-D histogram plot. In this example, the MAD plot 404 is displayed using a predetermined level and window attenuation value settings to visually emphasize details for particular tissue of interest. A clusters 406 represent air-like material and clusters 408 represents tissue/fat-like material. A magnified view 410 is shown for the region 412.

Figure 5:
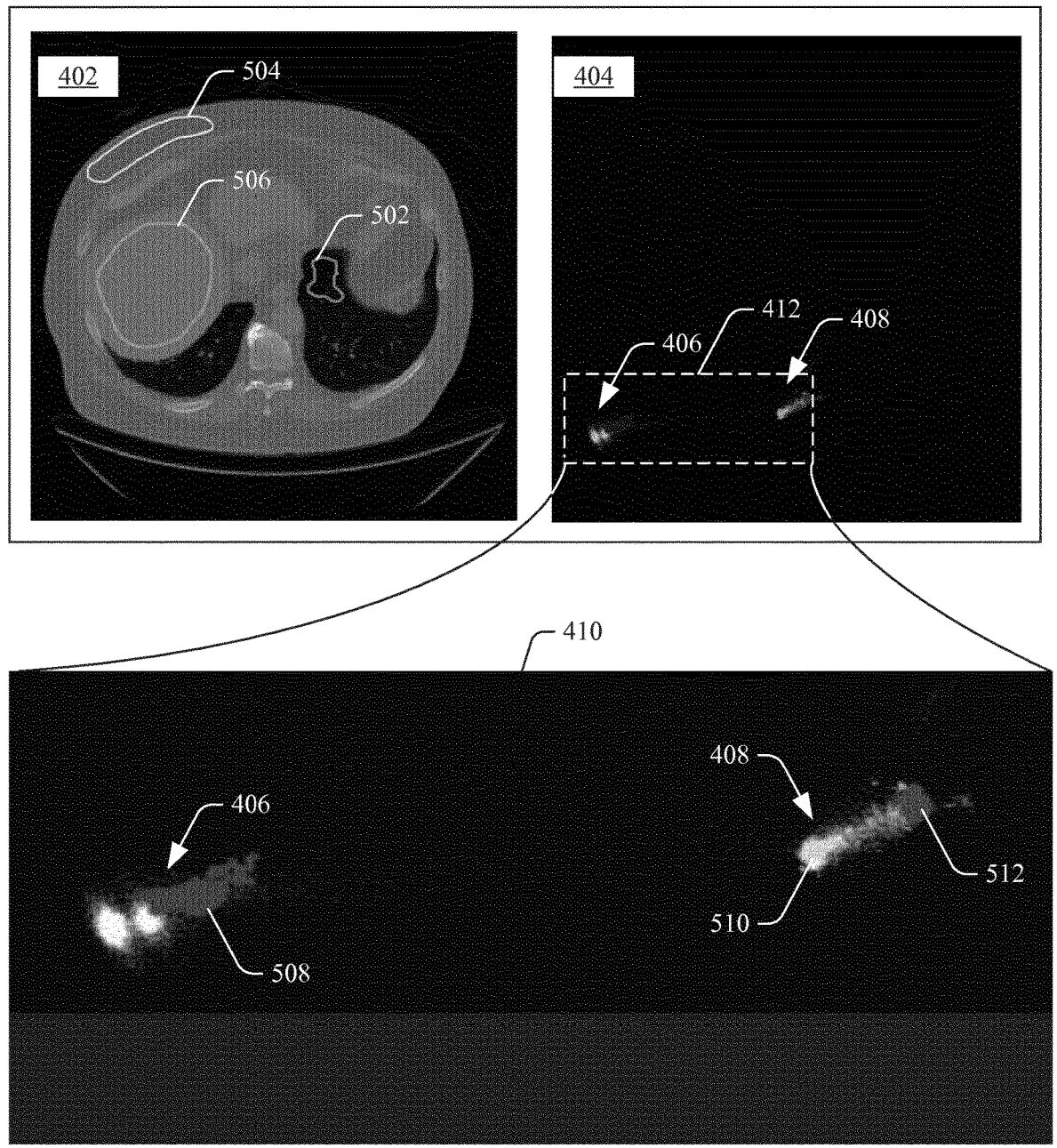
FIG. 5 depicts the 2-D image of FIG. 4 with ROI's identified therein and an updated MAD plot highlighting clusters corresponding to the materials in the ROI's.

In FIG. 5, regions of interest (ROI's) 502, 504 and 506 are indentified on the 2-D image 402. The ROI 502 includes lung tissue, the ROI 504 includes subcutaneous adipose tissue, and the RIO 506 includes liver tissue. These ROI's can be automatically identified (with user approval, rejection or modification), semi-automatically identified through system and user operations, or manually by the user, e.g., via software and an input device 124 such as a mouse. The illustrated shapes are not limiting. Other shapes, including predetermined shapes like a square, rectangle, circle, etc. are also contemplated herein.

In response to the identification of the ROI's 502, 504 and 506 on the 2-D image 402, the MAP plot 404 is updated to visually emphasive portions of the clusters 406 and 408 which correspond to the ROI's 502, 504 and 506. The emphasis can be through color, gray level, outlide, highlight, etc. In FIG. 5, the emphasis is shown through the magnified view 410 through gray level, with first highlighting 508 corresponding to the ROI 502 (lung tissue), second highlighting 510 corresponding to the ROI 504 (adipose tissue), and third highlighting 512 corresponding to the ROI 506 (liver tissue). The the ROI 508 is smeared due to partial volume effects with air and lung tissue.

Figure 6:
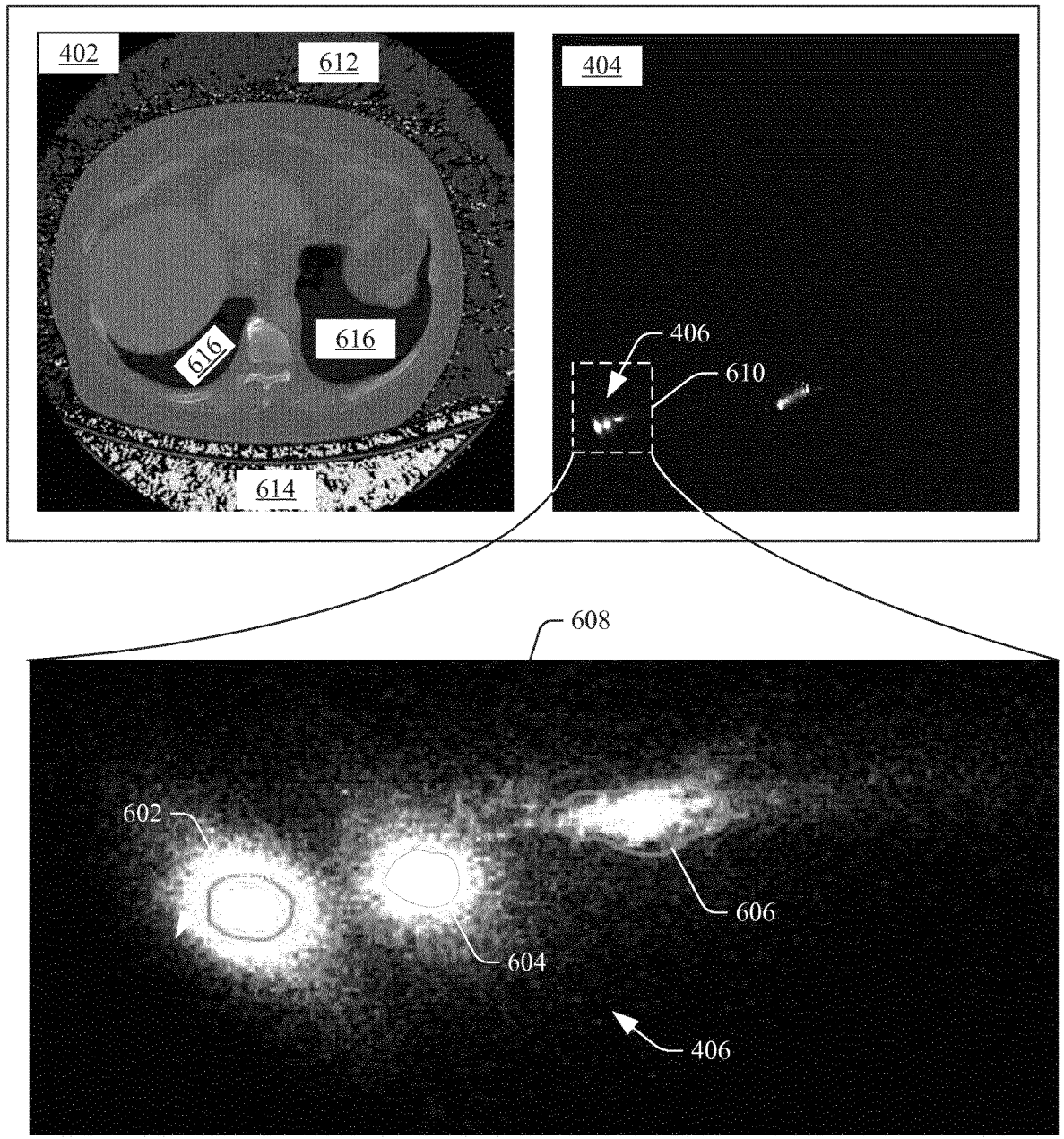
FIG. 6 depicts the MAD plot of FIG. 4 with ROI's identified therein for a first region and an updated 2-D image highlighting pixels or voxels corresponding to the materials represented in the ROI's.

In FIG. 6, ROI's 602, 604 and 606 are indentified on the MAD plot 404. Likewise, the ROI's 602, 604 and 606 can be, semi-automatically or manually identified. In one instance, one or more of the ROI's 602, 604 and 606 may correspond to known tissue that is to be visualized in the image 402. In another instance, the ROI's correspond to unknown tissue. A magnified view 608 of the clusters 406 (FIG. 4) for the air-like material is for a region 610.

The region 610 can be identified in the MAD plot 404 by comparing the MAD plot 404 with a MAD plot for the tissue of interest. Since a MAD plot provides a fingerprint for the tissue, a region in the MAD plot 404 matching a region in a MAD plot for tissue identifies the region in the MAD plot 404 for that tissue. An ROI can then be placed on the matching region. Where there is no matching MAD plot or the user wants to see what anatomy corresponds to particular region of the MAD plot, an ROI can be placed on the region. In FIG. 6, the ROI's 602, 604 and 606 correspond to air, bedfoam and lungs.

In response to the identification of the ROI's 602, 604 and 606 on the MAD plot 404, the 2-D image 402 is updated to visually emphasive portions of the 2-D image 402 which correspond to the ROI's 602, 604 and 606. Likewise, the emphasis can be through color, gray level, outlide, highlight, etc. In FIG. 6, the emphasis is shown through gray level, with first highlighting 612 corresponding to the ROI 602 (air), second highlighting 614 corresponding to the ROI 604 (bedfoam), and third highlighting 616 corresponding to the ROI 606 (lung).

If the user desires to see an image specific to a material corresponding to a ROI in the MAD plot 404, a suitable material decomposition can be created for that material, and the reconstructor 116 can process the received N energy projection data using that material decomposition. For example, a MAD plot may be used to identify pixels or voxels corresponding to a silicon breast implant by identifying a cluster for silicon in a MAD plot. The cluster can be identified, and then a silicon basis image can be generated, silicon in a conventional non-spectral image can be highlighted, etc.

Figure 7:
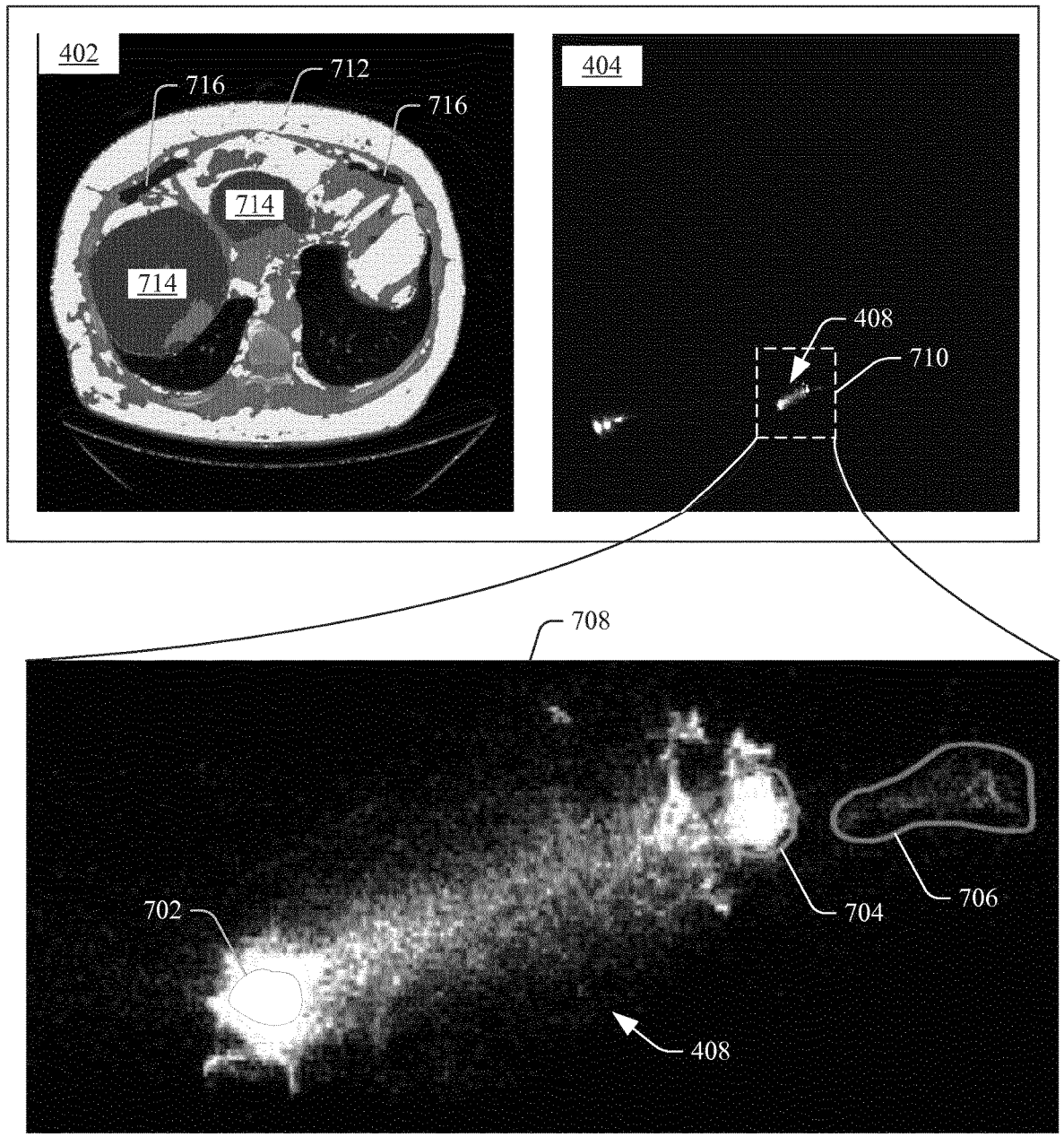
FIG. 7 depicts the MAD plot of FIG. 4 with ROI's identified therein for a second different region and an updated 2-D image highlighting pixels or voxels corresponding to the materials represented in the ROI's.

In FIG. 7, ROI's 702, 704 and 706 are indentified on the MAD plot 404. Likewise, the ROI's 702, 704 and 706 can be, semi-automatically or manually identified. In one instance, one or more of the ROI's 702, 704 and 706 may correspond to known tissue that is to be visuallized in the image 402. A magnified view 708 of the clusters 408 (FIG. 4) for the tissue/fat-like material is for a region 710. The region 710 can be identified in the MAD plot 404 by comparing the MAD plot 404 with a MAD plot for the tissue of interest.

In FIG. 7, the ROI's 702, 704 and 706 correspond to adipose tissue, liver tissue and rib cartilage. In response to the identification of the ROI's 702, 704 and 706 on the MAD plot 404, the 2-D image 402 is updated with the with first highlighting 712 corresponding to the ROI 702 (adipose tissue), second highlighting 714 corresponding to the ROI 704 (liver tissue), and third highlighting 716 corresponding to the ROI 706 (rib cartilage). Likewise, the emphasis can be through color, gray level, outlide, highlight, etc.

As shown in FIGS. 4-7, and described herein, the locations of pixels in the MAD plots depend on known properties (i.e., the coefficients of attenuation for the photoelectric effect and Compton scattering) of tissues and elements within the human body. These locations occupy a small fraction of the entire MAD plot. Any pixels outside of these ranges arise either from foreign objects or materials within the body (i.e., metal appliances or silicone implants) or from artifacts due to errors in signal acquisition or image reconstruction. The precise patterns and/or the positions of these artifacts can provide clues regarding their origin and nature. Thus MAD plots could provide a tool for both assessing and improving scanner performance.

FIGS. 8-14 presents various methods in connection with a MAD plot described herein. It is to be appreciated that the ordering of the acts in the method is not limiting. As such, other orderings are contemplated herein. In addition, one or more acts may be omitted and/or one or more additional acts may be included.

Figure 8:
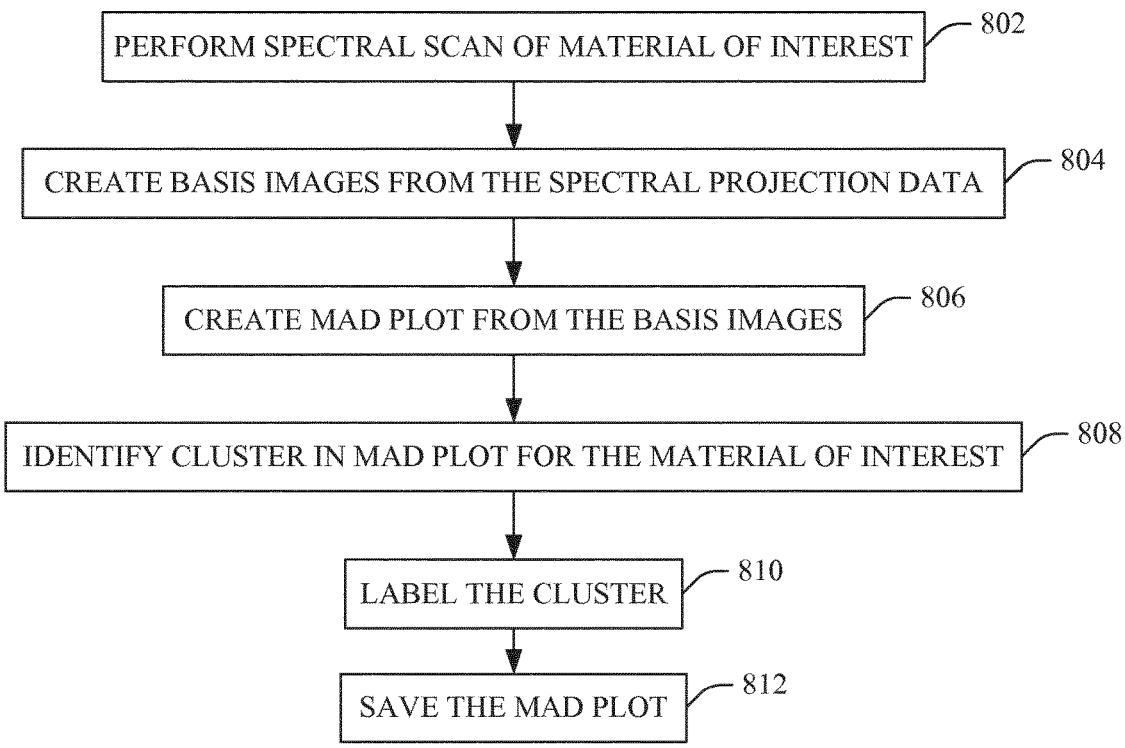
FIG. 8 illustrates an example method for creating a spectral CT fingerprint in connection with multi-energy projection data.

FIG. 8 illustrates an example method for creating a spectral CT fingerprint in connection with a multi-energy projection data.

At 802, a spectral scan of a subject or object including a material of interest (MOI) is performed, creating multi-energy projection data, each set of projection data corresponding to a different energy.

At 804, a plurality of basis images is generated with the multi-energy projection data, each basis image corresponding to a different energy.

At 806, a MAD plot is created from the plurality of basis images.

At 808, a cluster in the MAD plot corresponding to the material of interest is identified in the MAD plot. This can be achieved using known photo-electric effect and Compton scatter attenuation coefficients from the literature and/or otherwise, data from previous scans with and without the material interest, and/or otherwise.

At 810, the cluster is labeled to associate the cluster with the material of interest.

At 812, the MAD plot is saved, e.g., to computer memory for use.

Figure 9:
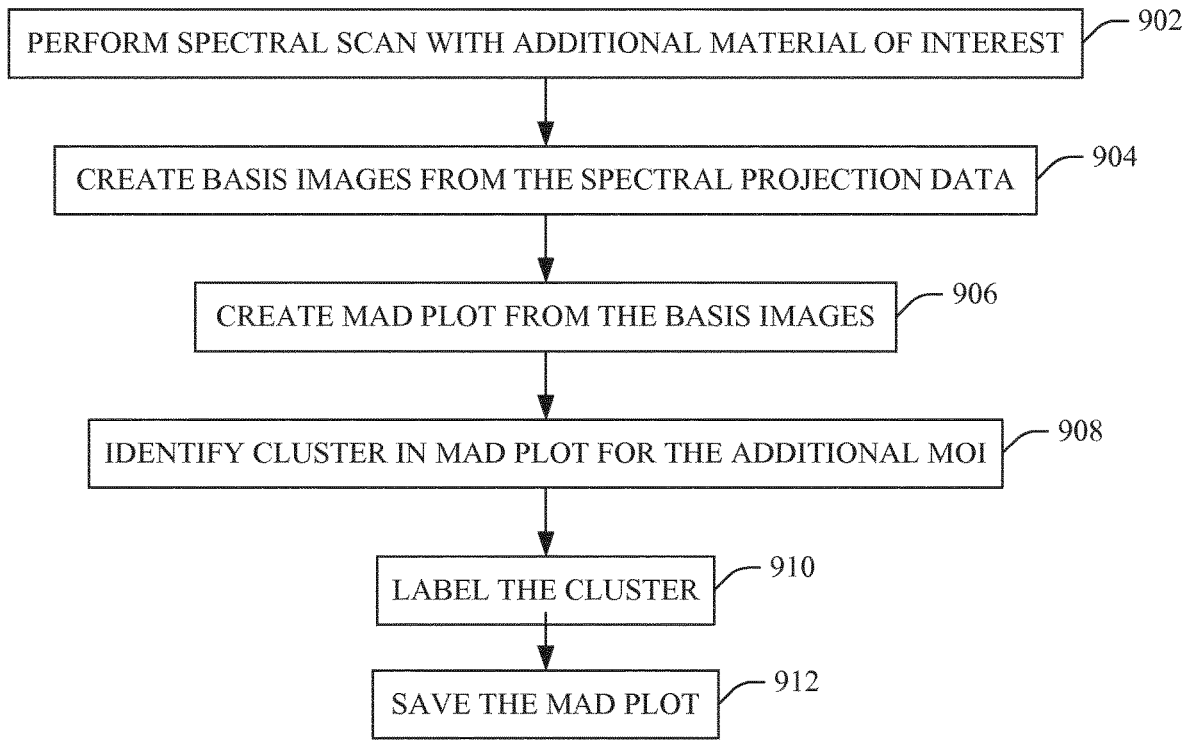
FIG. 9 illustrates another example method for creating a spectral CT fingerprint in connection with multi-energy projection data.

FIG. 9 illustrates another example method for creating a spectral CT fingerprint in connection with a multi-energy projection data.

At 902, a spectral scan of a subject or object including a material of interest in addition to the material of interest in FIG. 8 is performed, creating multi-energy projection data.

At 904, a plurality of basis images is generated with the multi-energy projection data as described herein.

At 906, a MAD plot is created from the plurality of basis images.

At 908, a cluster in the MAD plot corresponding to the different material of interest is located in the MAD plot by comparing the MAD plot with the stored MAD plot from FIG. 8 to locate a cluster in the MAD plot that is not in the stored MAD plot.

At 910, the cluster is labeled to associate the cluster with the different material of interest.

At 912, the MAD plot is saved.

Figure 10:
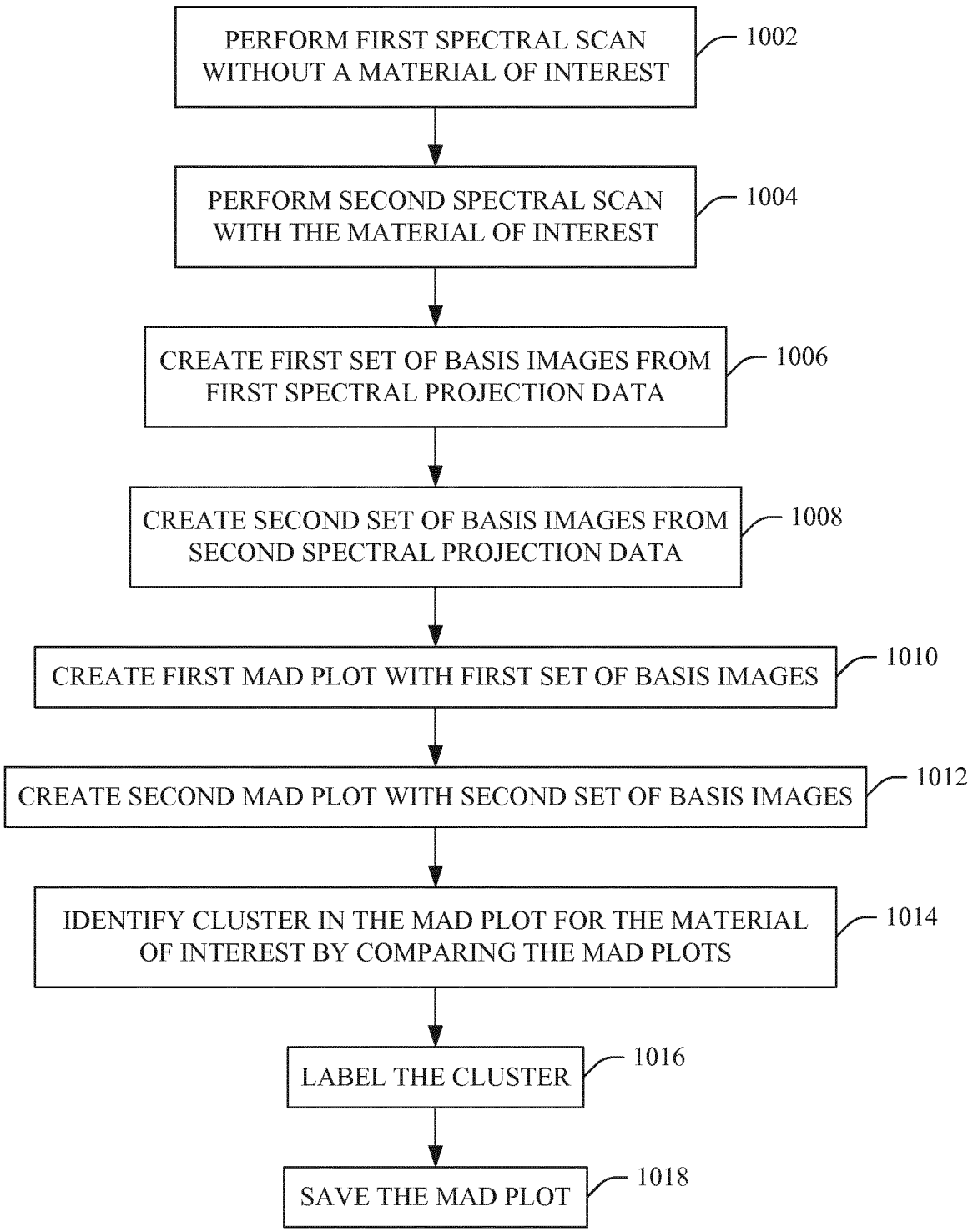
FIG. 10 illustrates yet another example method for creating a spectral CT fingerprint in connection with multi-energy projection data.

FIG. 10 illustrates another example method for creating a spectral CT fingerprint in connection with a multi-energy projection data.

At 1002, a first spectral scan of a first subject or object including without a material of interest is performed, creating first projection data.

At 1004, a second spectral scan of a second subject or object including with the material of interest is performed, creating second projection data.

The projection data of acts 1002 and 1004 can be newly acquired projection data and/or projection data mined from previous examinations. Furthermore, act 1004 can be before act 1002.

At 1006, a first plurality of basis images is generated with the first projection data.

At 1008, a second plurality of basis images is generated with the second projection data.

At 1010, a first MAD plot is created from the first plurality of basis images.

At 1012, a second MAD plot is created from the second plurality of basis images.

At 1014, a cluster in the first MAD plot corresponding to the material of interest is located by comparing the first and second MAD plots to locate a cluster in the first MAD plot that is absent from the second MAD plot.

At 1016, the cluster is labeled to associate the cluster with the material of interest.

At 1018, the first MAD plot is saved.

Figure 11:
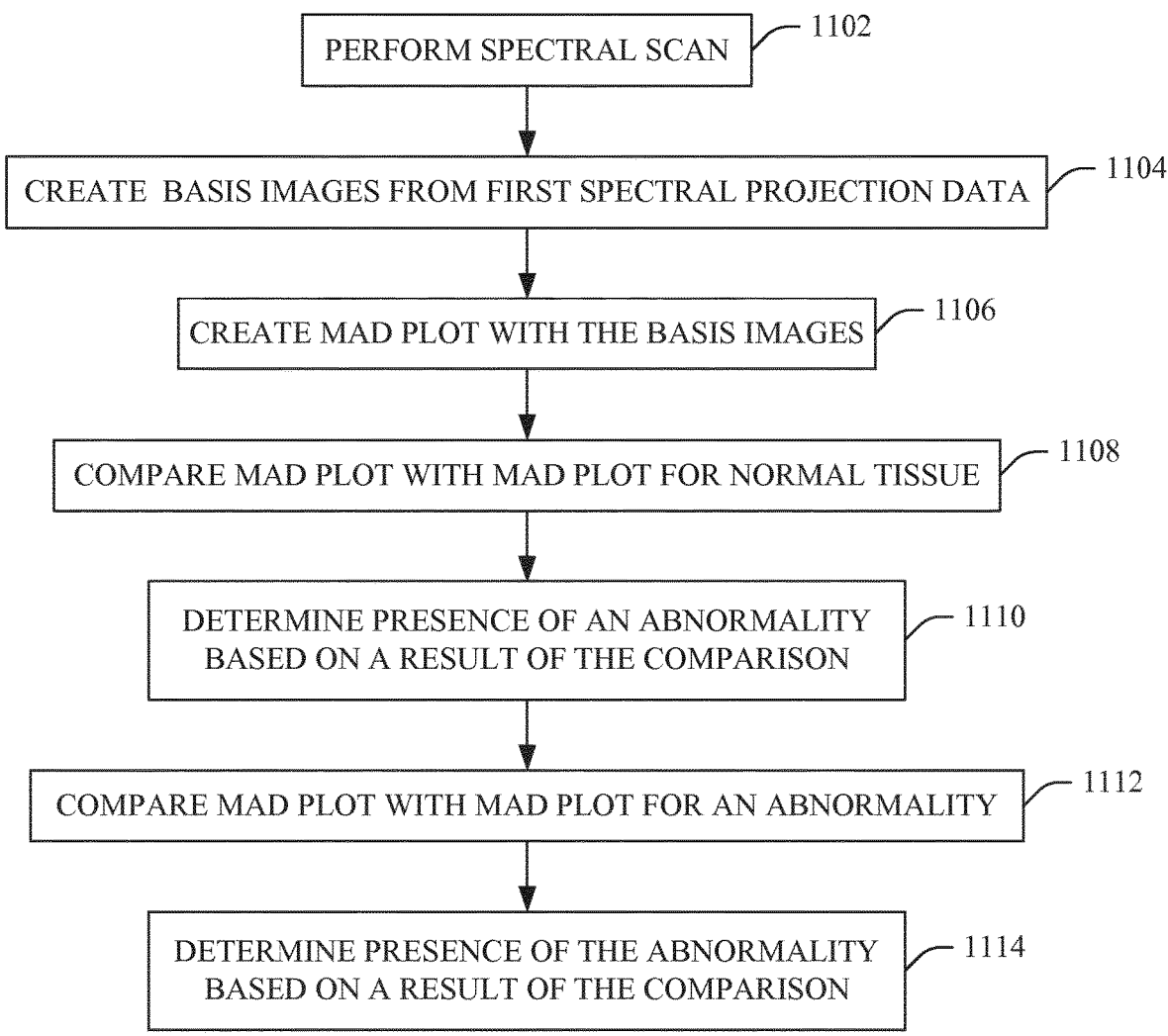
FIG. 11 illustrates example method for identifying a presence and/or a type of abnormality in connection with multi-energy projection data.

FIG. 11 illustrates example method for identifying a presence and/or a type of abnormality in connection with a multi-energy projection data.

At 1102, a spectral scan of a subject is performed, creating projection data.

At 1104, a plurality of basis images is generated with the projection data.

At 1106, a MAD plot is created from the plurality of basis images.

At 1108, the MAD plot is compared with a MAD plot for normal tissue.

At 1110, it is determined the subject has an abnormality in response to the MAD plot including a cluster that is absent from the MAD plot for the normal tissue.

At 1112, the MAD plot is compared with a MAD plot for an abnormality.

At 1114, it is determined the subject has the abnormality in response to the MAD plot including a cluster that matches a cluster representing the abnormality in the MAD plot for the abnormality.

In a variation, acts 1108 and 1110 are omitted and the MAD plot is compared only with the MAD plot for the abnormality. In another variation, acts 1112 and 1114 are omitted and the MAD plot is compared only with the MAD plot for the normal tissue.

Figure 12:
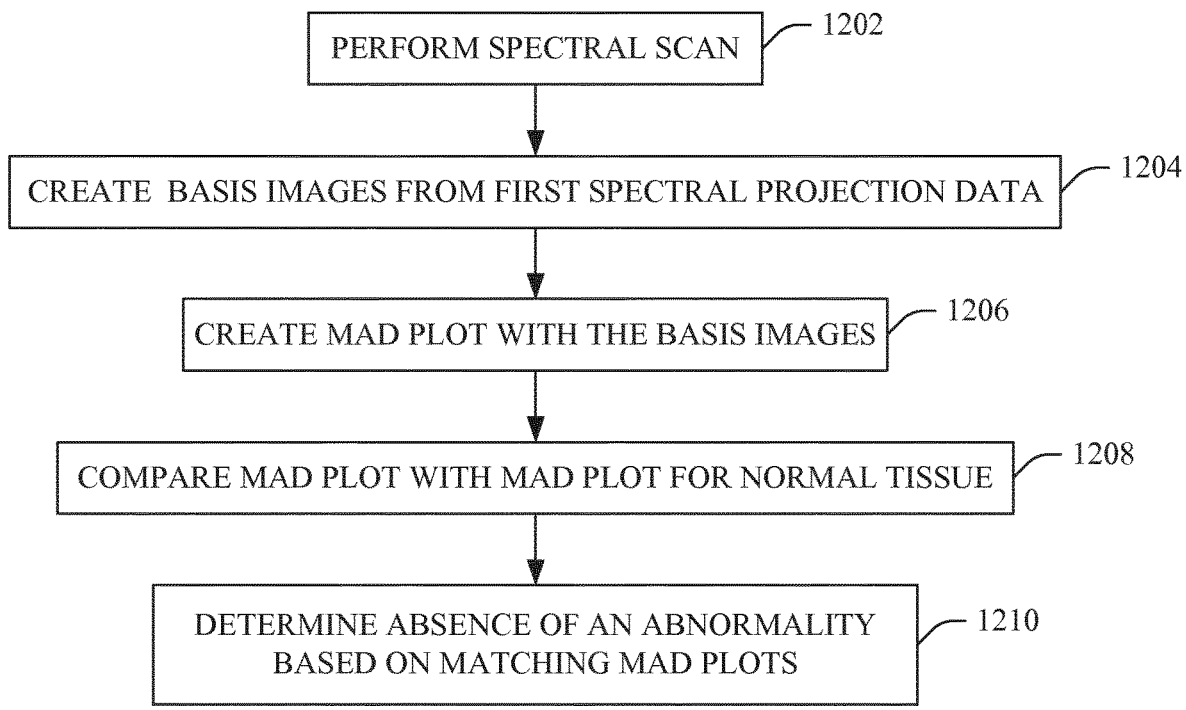
FIG. 12 illustrates example method for identifying an absence of an abnormality in connection with multi-energy projection data.

FIG. 12 illustrates example method for identifying an absence of an abnormality in connection with a multi-energy projection data.

At 1202, a spectral scan of a subject is performed, creating projection data.

At 1204, a plurality of basis images is generated with the projection data.

At 1206, a MAD plot is created from the plurality of basis images.

At 1208, the MAD plot is compared with a MAD plot for the normal tissue.

At 1210, it is determined the subject does not have an abnormality in response to the MAD plot matching the MAD plot for the normal tissue.

Figure 13:
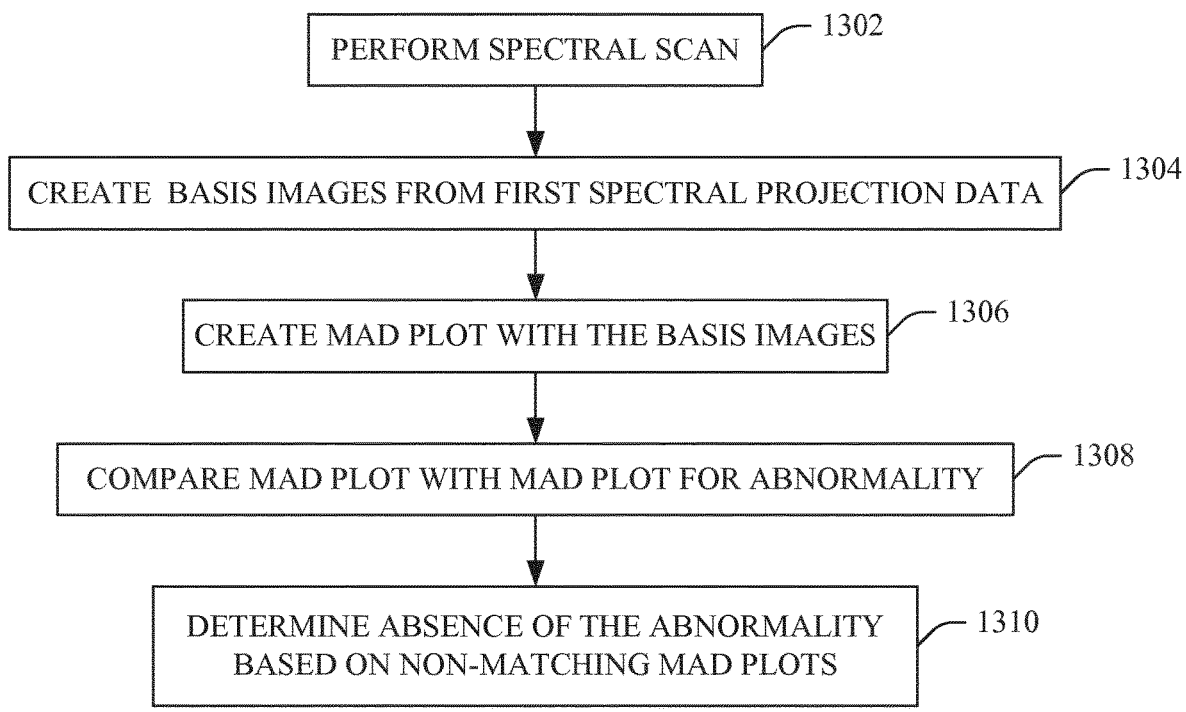
FIG. 13 illustrates another example method for identifying an absence of an abnormality in connection with multi-energy projection data.

FIG. 13 illustrates example method for identifying an absence of an abnormality in connection with a multi-energy projection data.

At 1302, a spectral scan of a subject is performed, creating projection data.

At 1304, a plurality of basis images is generated with the projection data.

At 1306, a MAD plot is created from the plurality of basis images.

At 1308, the MAD plot is compared with a MAD plot for an abnormality.

At 1310, it is determined the subject does not have the abnormality in response to the MAD plot including a cluster that matches a cluster representing the abnormality in the MAD plot for the abnormality.

Figure 14:
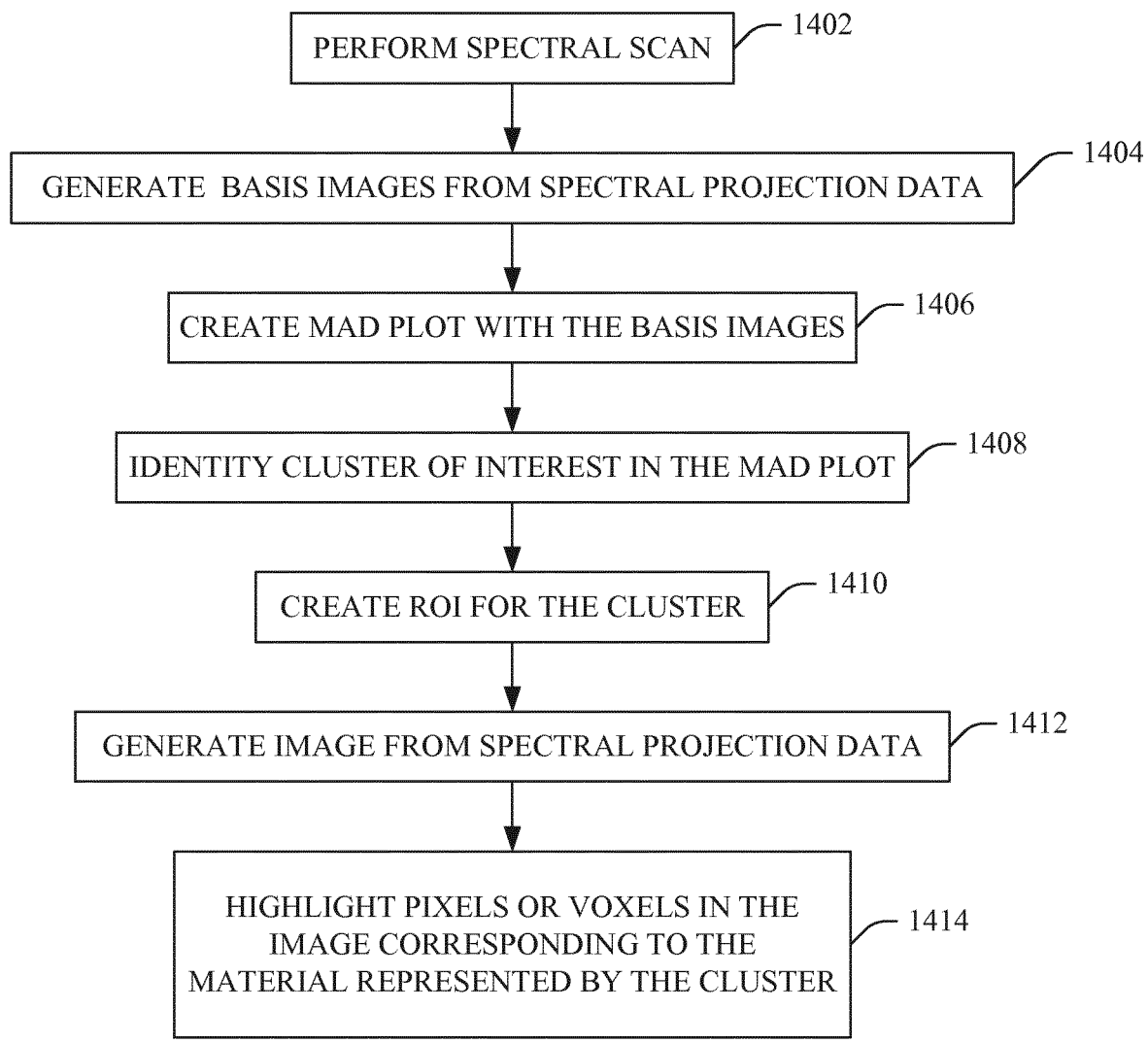
FIG. 14 illustrate example method for visualizing tissue of interest in an image in connection with multi-energy projection data.

FIG. 14 illustrates example method for visualizing tissue of interest in an image in connection with a multi-energy projection data.

At 1402, a spectral scan of a subject is performed, creating projection data.

At 1404, a plurality of basis images is generated with the projection data.

At 1406, a MAD plot is created from the plurality of basis images.

At 1408, a cluster of the MAD plot corresponding to the tissue of interest is identified. This can be achieved by comparing the MAD plot with a MAD plot for the tissue of interest and/or otherwise.

At 1410, a ROI is created for the cluster.

At 1412, an image is generated with the projection data.

At 1414, pixels or voxels corresponding to the tissue of interest are highlighted in the image for the material represented by the cluster.

Figure 15:
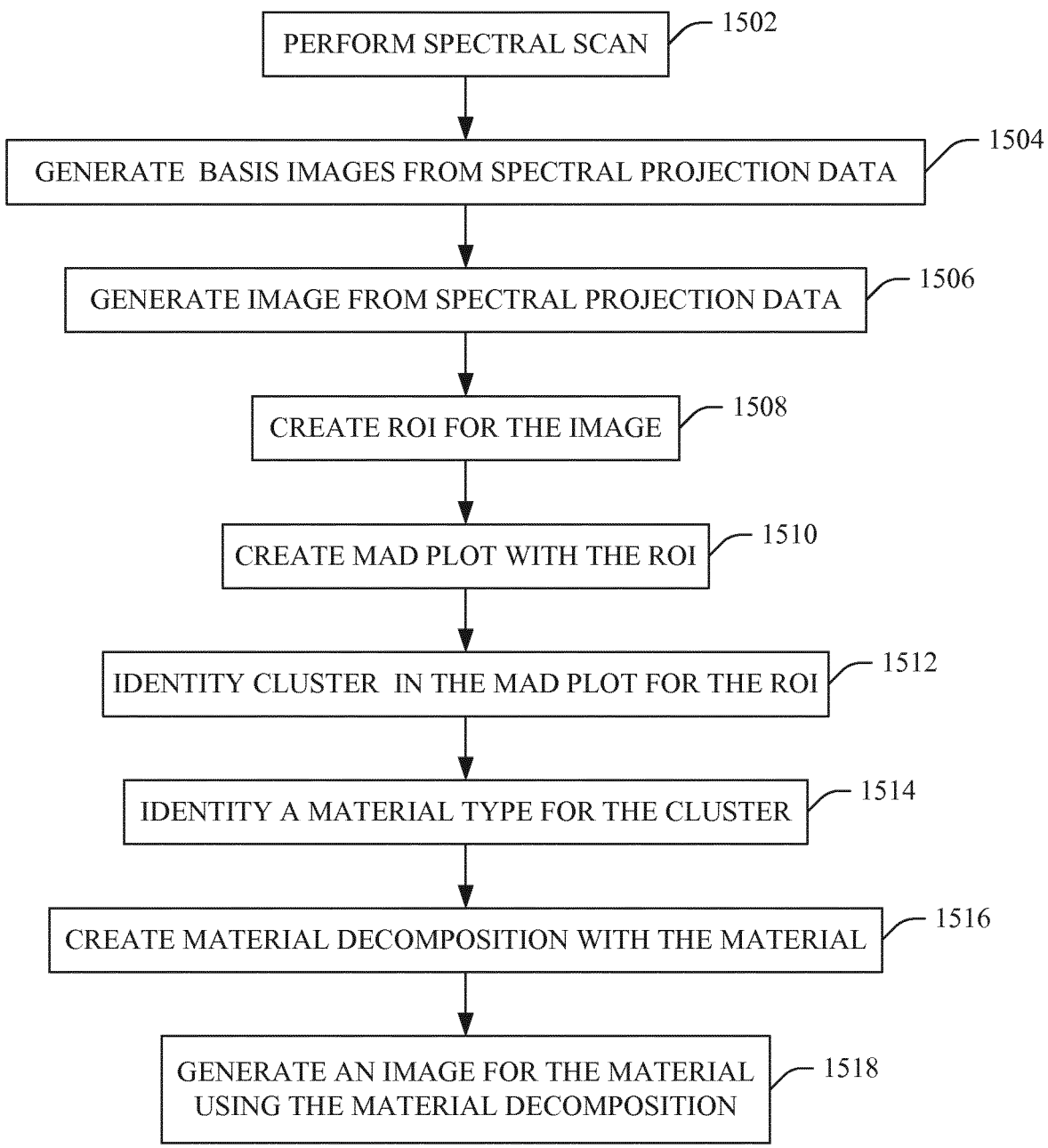
FIG. 15 illustrate example method for identifying tissue of interest in an image in connection with multi-energy projection data.

FIG. 15 illustrates example method for identifying tissue of interest in an image in connection with a multi-energy projection data.

At 1502, a spectral scan of a subject is performed, creating projection data.

At 1504, a plurality of basis images is generated with the projection data.

At 1506, an image is generated with the projection data.

At 1508, an ROI is created in the image.

At 1510, a MAD plot is created for the ROI.

At 1512, a cluster of the MAD plot corresponding to the ROI is identified.

At 1514, a type material in the ROI is identified by the cluster. This can be achieved by comparing the MAD plot with MAD plots for different types of materials and/or otherwise.

At 1516, a material decomposition is created with the identified material.

At 1518, a spectral image for the material is generated using the material decomposition.

The acts herein may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium.

Figure 16:
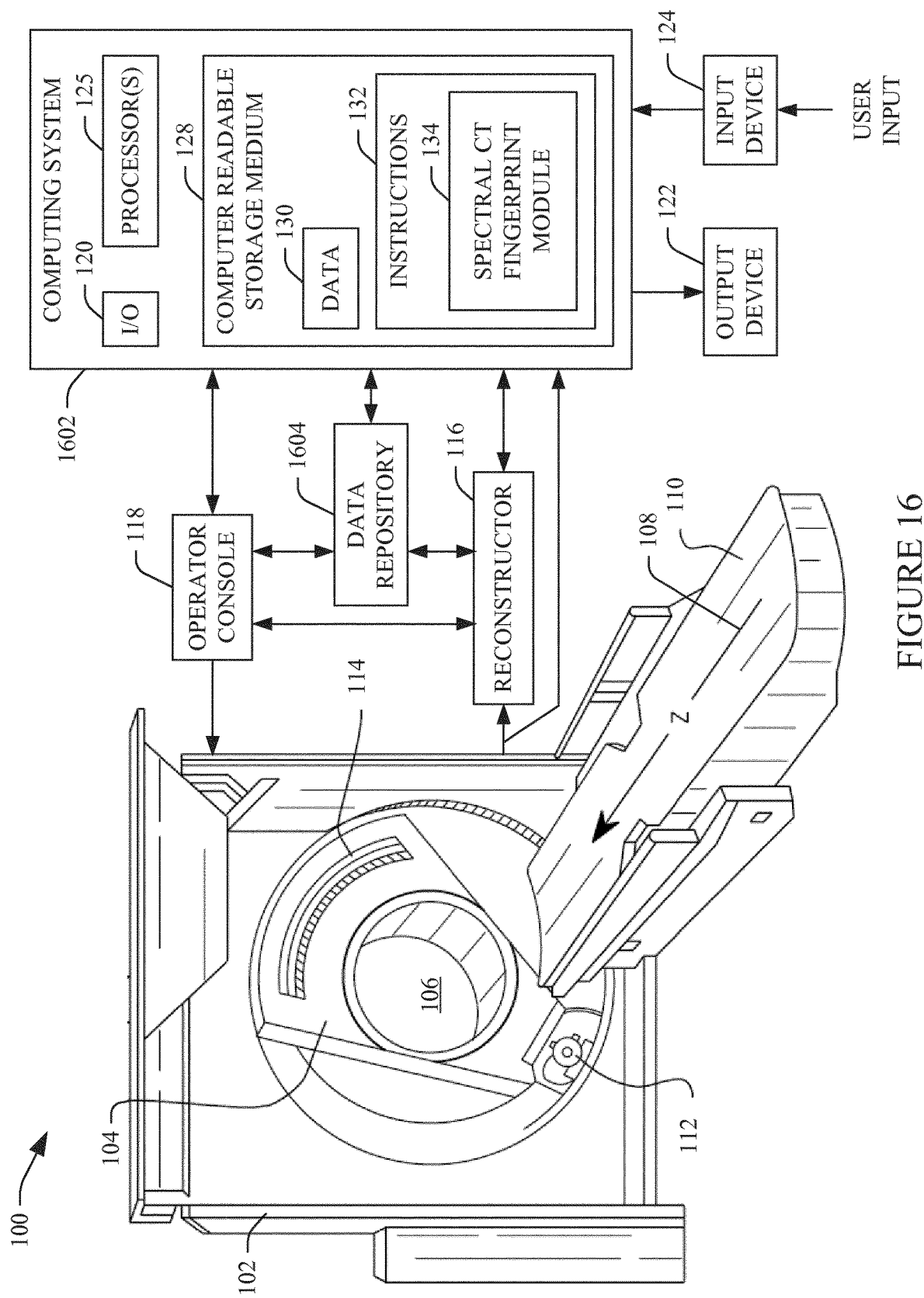
FIG. 16 schematically illustrates a variation of FIG. 1 in which the spectral CT fingerprint module is part of a system remote from the imaging system.

FIG. 16 schematically illustrates a variation of FIG. 1 in which the components of the operator console 118 related to the spectral CT fingerprint module 132 are part of a computing system 1602, which is a separate apparatus from the imaging system 100. The operator console 118 includes a human readable output device such as a monitor or display and an input device such as a keyboard and mouse, and software resident on the console 118 allows the operator to interact with the scanner 100. The instructions 130 include a reconstructor to reconstruct volumetric image data.

The computing system 160 can receive projection from the imaging system 100 (the console 118 and/or the reconstructor 116), a data repository 1604, another imaging system, and/or other device. An example of suitable data repository 1604 is a picture archiving and communication system (PACS), a radiology information system (RIS), a hospital information system (HIS), an electronic medical record (EMR), a database, a server, an imaging system, and/or other data repository.

The MAD plot discussed herein can also be used for quality assurance. For example, since a MAD plot for a particular material is independent of the X-ray source and the detector array, a plurality of imaging system can be tested by scanning a phantom including a particular material, generating a MAD plot for each imaging system for that material, and comparing the MAD plots with a known valid reference MAD plot(s) for that material. If a MAD plot for an imaging system deviates from the reference MAD plot(s), the imaging system, e.g., can be re-calibrated.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
  generating, with an imaging system, spectral projection data of a subject, including at least first spectral projection data corresponding to a first energy range and second spectral projection data corresponding to a second energy range, wherein the first and the second energy range are different;
  constructing an image from a combination of the spectral projection data;
  constructing a set of basis images for the energy ranges and from the spectral projection data;
  constructing a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data;
  visually displaying, concurrently, the image and the multi-dimensional histogram;
  comparing the displayed multi-dimensional histogram with a multi-dimensional histogram for known normal tissue and/or with a multi-dimensional histogram for known abnormal tissue; and
  depending on the comparison result determining a presence of an abnormality in the displayed multi-dimensional histogram.

2. The method of claim 1, further comprising:
  identifying the presence of an abnormality in the displayed multi-dimensional histogram in response to a cluster in the displayed multi-dimensional histogram being absent in the multi-dimensional histogram for known normal tissue.

3. The method of claim 2, further comprising:
  cluster to a cluster of the multi-dimensional histogram corresponding to the known abnormal tissue;
  identifying the presence of the known abnormal tissue by matching the cluster to a cluster of the multi-dimensional histogram corresponding to the known abnormal tissue.

4. The method of claim 1, further comprising:
  dimensional histogram in response to a cluster in the displayed multi-dimensional histogram being absent in the multi-dimensional histogram for known normal tissue;
  identifying the presence of the known abnormal tissue in the displayed multi-dimensional histogram in response to a cluster in the displayed multi-dimensional histogram being absent in the multi-dimensional histogram for known normal tissue.

5. The method of claim 1, further comprising:
  absent from the multi-dimensional histogram for known normal tissue;
  identifying the cluster in the displayed multi-dimensional histogram that is absent from the multi-dimensional histogram for known normal tissue.

6. The method of claim 1, further comprising:
  receiving an input identifying a region of interest for a cluster in the multi-dimensional histogram; and
  updating the displayed image to highlight a group of pixels or voxels of the image corresponding to a material in the identified region of interest in the multi-dimensional histogram.

7. The method of claim 1, further comprising:
  receiving an input identifying a region of interest in the image; and
  updating the displayed multi-dimensional histogram to highlight a cluster of the set of clusters corresponding to a material in the identified region of interest in the image.

8. The method of claim 7, further comprising:
  comparing the highlighted multi-dimensional histogram with a library of multi-dimensional histograms for different materials;
  matching the highlighted cluster with a cluster in a multi-dimensional histogram from the library; and
  identifying a type of the material based on the multi-dimensional histogram corresponding to the matched cluster.

9. The method of claim 8, further comprising:
creating a material decomposition for the material type; and
constructing a spectral image of the material type using the material decomposition.

10. The method of claim 1, further comprising:
comparing the displayed multi-dimensional histogram with a library of multi-dimensional histograms for a plurality of materials; and
identifying a type of material represented by the cluster by matching the cluster to a cluster in one of the histograms from the library of multi-dimensional histograms.

11. The method of claim 10, wherein the cluster corresponds to a known material, and further comprising:
labelling the cluster as representing the known material; and
saving the displayed multi-dimensional histogram to the library.

12. A system, comprising:
a memory storing instructions, including a spectral CT fingerprint module; and
processor circuitry configured to execute at least instructions corresponding to the spectral CT fingerprint module, which causes the processor circuitry to:
generate spectral projection data of a subject, including at least first spectral projection data corresponding to a first energy range and second spectral projection data corresponding to a second energy range, wherein the first and the second energy range are different;
construct an image from a combination of the spectral projection data;
construct a set of basis images for the energy ranges and from the spectral projection data;
construct a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data;
visually display, concurrently, the image and the multi-dimensional histogram;
compare the displayed multi-dimensional histogram with a multi-dimensional histogram for known normal tissue and/or with a multi-dimensional histogram for known abnormal tissue; and
depending on the comparison result, determine a presence of an abnormality in the displayed multi-dimensional histogram.

13. The system of claim 12, wherein the processor circuitry is configured to receive an input identifying a region of interest for a cluster in the multi-dimensional histogram, and to update the displayed image to highlight a group of pixels or voxels of the image corresponding to a material in the identified region of interest in the multi-dimensional histogram.

14. The system of claim 12, wherein the processor is configured to receive an input identifying a region of interest in the image, and to update the displayed multi-dimensional histogram to highlight a cluster of the set of clusters corresponding to a material in the identified region of interest in the image.

15. The system of claim 14, wherein the processor circuitry is configured to compare the highlighted multi-dimensional histogram with a library of multi-dimensional histograms for different materials, to match the highlighted cluster with a cluster in a multi-dimensional histogram from the library, and to identify a type of the material based on the multi-dimensional histogram corresponding to the matched cluster.

16. The system of claim 15, wherein the processor circuitry is configured to create a material decomposition for the material type, and to construct a spectral image of the material type using the material decomposition.

17. The system of claim 12, wherein the processor circuitry is configured to compare the displayed multi-dimensional histogram with a multi-dimensional histogram for known normal tissue, and to identify a presence of an abnormality in the displayed multi-dimensional histogram in response to a cluster in the displayed multi-dimensional histogram being absent in the multi-dimensional histogram for known normal tissue.

18. The system of claim 17, wherein the processor circuitry is configured to identify a presence of the known abnormal tissue by matching the cluster to a cluster of the multi-dimensional histogram corresponding to the known abnormal tissue.

19. The system of claim 12, wherein the processor circuitry is configured to identify a presence of the known abnormal tissue in the displayed multi-dimensional histogram in response to a cluster in the displayed multi-dimensional histogram being absent in the multi-dimensional histogram for known normal tissue.

20. The system of claim 12, wherein the processor circuitry is configured to identify a cluster in the displayed multi-dimensional histogram that is absent from the multi-dimensional histogram for known normal tissue.

21. The system of claim 12, wherein the processor circuitry is configured to identify a type of material represented by the cluster by matching the cluster to a cluster in one of the histograms from the library of multi-dimensional histograms.

22. The system of claim 21, wherein the cluster corresponds to a known material, and the processor labels the cluster as representing the known material, and saves the displayed multi-dimensional histogram to the library.

23. A non-transitory computer readable medium encoded with computer executable instructions, which, when executed by processor circuitry, cause the processor circuitry to:
generate spectral projection data of a subject, including at least first spectral projection data corresponding to a first energy range and second spectral projection data corresponding to a second energy range, wherein the first and the second energy range are different;
construct an image from a combination of the spectral projection data;
construct a set of basis images for the energy ranges and from the spectral projection data;
construct a multi-dimensional histogram from the set of basis images, wherein the multi-dimensional histogram includes at least two axes, a first corresponding to a first basis component and a second corresponding to a second basis component, and the multi-dimensional histogram includes a set of clusters, including one cluster for each material represented in the spectral projection data;
visually display, concurrently, the image and the multi-dimensional histogram compare the displayed multi-dimensional histogram with a multi-dimensional histogram for known normal tissue and/or with a multi-dimensional histogram for known abnormal tissue; and depending on the comparison result, determine a presence of an abnormality in the displayed multi-dimensional histogram.

\* \* \* \* \*